(12) United States Patent
Evans et al.

(10) Patent No.: US 9,339,606 B2
(45) Date of Patent: May 17, 2016

(54) FOLDABLE FINGER FLANGE FOR A SYRINGE

(71) Applicant: West Pharmaceutical Services, Inc., Exton, PA (US)

(72) Inventors: Christopher Evans, Long Valley, NJ (US); Brian Costello, Whitehouse Station, NJ (US); Christopher Gieda, Long Valley, NJ (US); Raymond Protasiewicz, Whippany, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 14/278,651

(22) Filed: May 15, 2014

(65) Prior Publication Data

US 2015/0328408 A1    Nov. 19, 2015

(51) Int. Cl.
*A61M 5/31*    (2006.01)

(52) U.S. Cl.
CPC ..... *A61M 5/3137* (2013.01); *A61M 2005/3139* (2013.01)

(58) Field of Classification Search
CPC .................. A61M 5/3137; A61M 2005/3139
USPC .................................................. 604/187, 227
See application file for complete search history.

(56) References Cited

U.S. PATENT DOCUMENTS

| | | | |
|---|---|---|---|
| 5,925,032 A * | 7/1999 | Clements | 606/1 |
| 2005/0148944 A1* | 7/2005 | Hsieh et al. | 604/198 |
| 2011/0046559 A1* | 2/2011 | Lum et al. | 604/189 |
| 2012/0095438 A1 | 4/2012 | Lanin et al. | |

FOREIGN PATENT DOCUMENTS

| | | |
|---|---|---|
| JP | H09-173451 A | 7/1997 |
| WO | 2011021621 A1 | 2/2011 |
| WO | 2012154185 A1 | 11/2012 |

* cited by examiner

*Primary Examiner* — Bhisma Mehta
*Assistant Examiner* — James Ponton
(74) *Attorney, Agent, or Firm* — Panitch Schwarze Belisario & Nadel LLP

(57) ABSTRACT

A conventional syringe includes a syringe barrel having a syringe barrel flange laterally extending from an open proximal end of the syringe barrel and a syringe plunger for advancement into the syringe barrel through the open proximal end. A foldable finger flange for such a syringe comprises an attachment member configured to be removably mounted onto the syringe barrel flange, and a flange member pivotably attached to the attachment member. At least a portion of the flange member is pivotable between a use position, wherein said portion of the flange member extends generally perpendicular to the syringe barrel, thereby providing a flange having a greater extent than the syringe barrel flange, and a non-use position, wherein said portion of the flange member does not extend generally perpendicular to the syringe barrel.

18 Claims, 8 Drawing Sheets

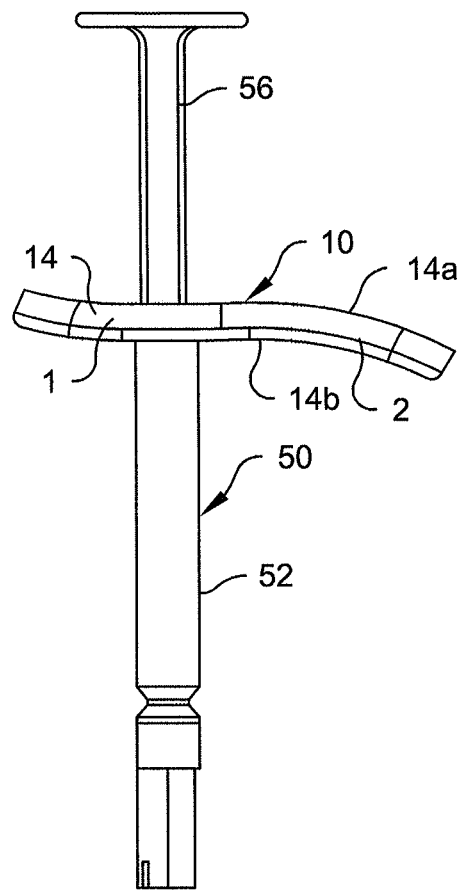
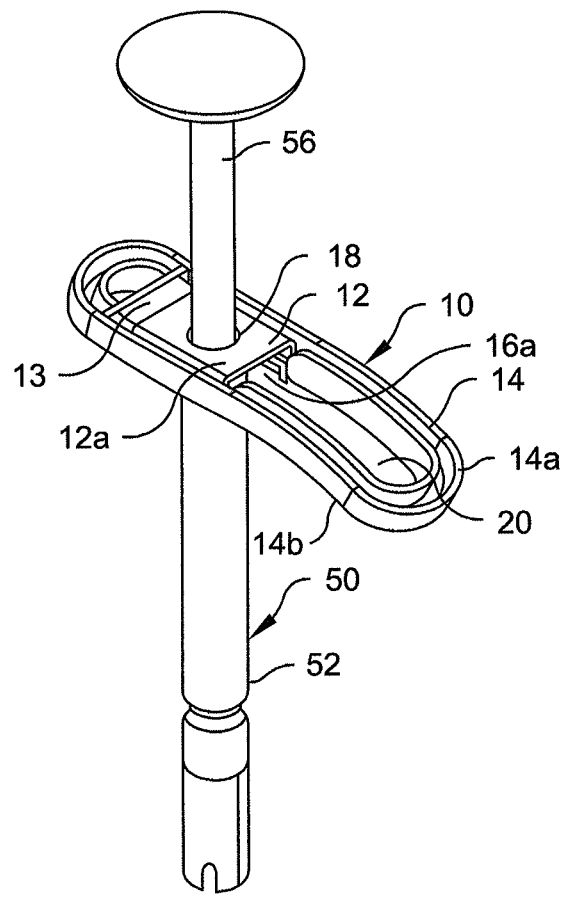
*Fig. 4a*  *Fig. 4b*

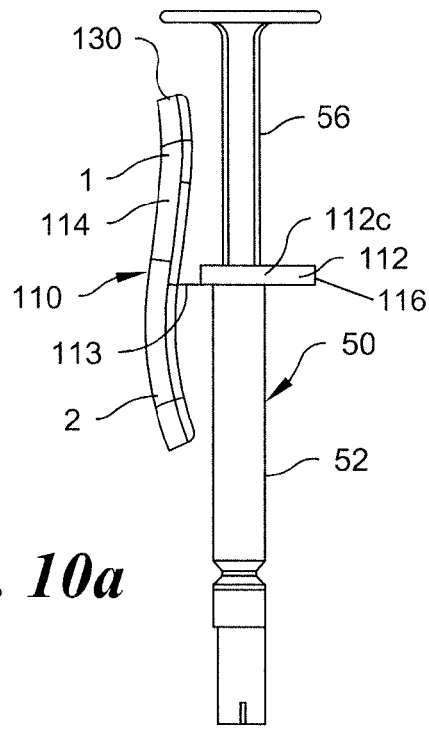
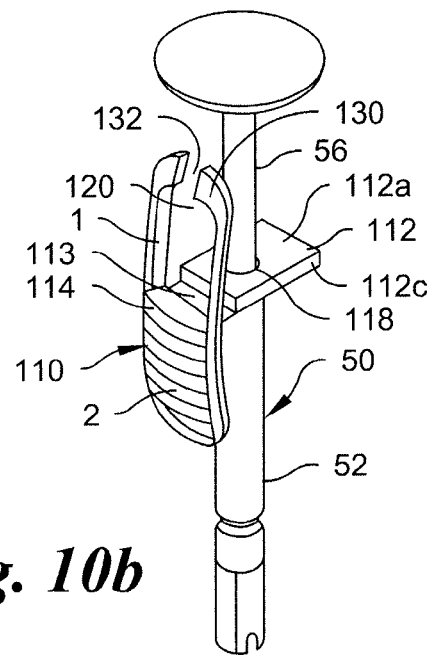
Fig. 10a    Fig. 10b
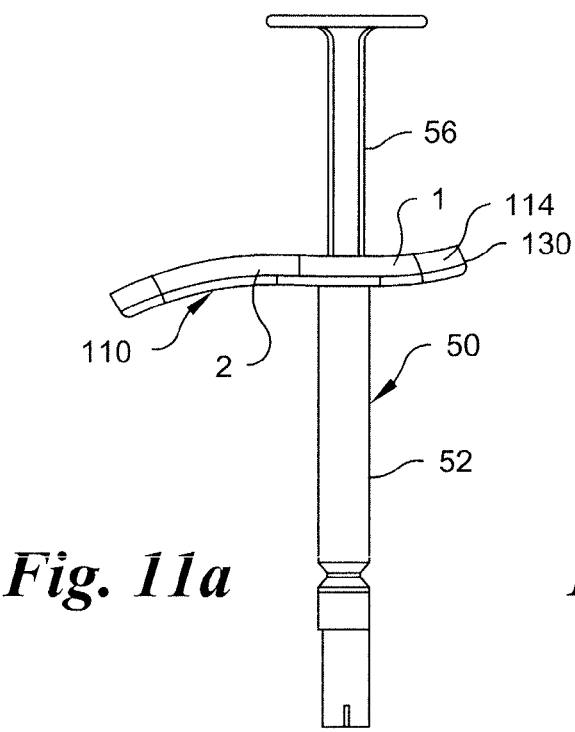
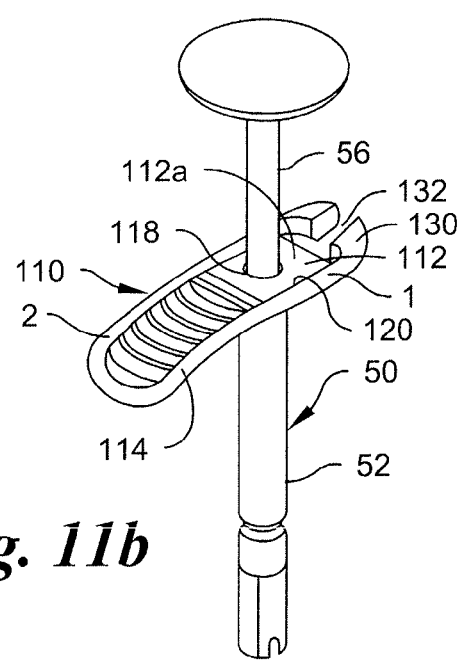
Fig. 11a    Fig. 11b

FOLDABLE FINGER FLANGE FOR A SYRINGE

BACKGROUND OF THE INVENTION

The present invention is generally directed to an accessory for a syringe, and more particularly to a finger flange removably mountable onto a syringe, and movable between a use position and a non-use position.

A syringe is a simple pump utilized for delivering or receiving a substance, e.g., medicament, to/from a recipient or a receptacle. Conventional syringes include a syringe barrel (for holding the substance) having a syringe barrel flange laterally extending from an open proximal end of the syringe barrel and a syringe plunger for advancement into the syringe barrel, or withdrawal through the syringe barrel, through the open proximal end. The syringe flange is often referred to as a "finger flange," because the flange provides a surface which a user can grip or engage with his/her fingers to hold the syringe barrel in place while advancing/retracting the syringe plunger through the barrel.

The size, shape and overall ergonomics of the syringe barrel finger flange can have a direct effect on usability, leverage and control over the syringe. The syringe barrel finger flange on a standard International Organization for Standardization ("ISO") 1 mL syringe can be inadequate in size, shape and ergonomics. Accordingly, typical finger flange accessories manufactured for removable or permanent mounting onto conventional syringes are larger in size for improved usability, leverage and control over the syringe. However, one drawback associated with such finger flange accessories is that the greater size of the finger flange accessory results in an increased packaging footprint when packaged with the syringe. As a result, there is a direct effect on cost, shipping, storage, etc., which ultimately translates into increased costs for end consumers.

Therefore, it would be advantageous to manufacture a foldable finger flange accessory for a syringe that has a geometry allowing the finger flange to be oriented in one more compact configuration during shipping/transport, i.e., non-use position, having a relatively decreased footprint, and reconfigurable into a use configuration, e.g., at the point of use, having a greater footprint for assisting in improved usability of the syringe. Such a device would provide a user with an improved syringe usage experience, while also minimizing the expense of increased packing size.

BRIEF SUMMARY OF THE INVENTION

Briefly stated, one aspect of the present invention is directed to a foldable finger flange for a syringe. The syringe includes a syringe barrel having a syringe barrel flange laterally extending from an open proximal end of the syringe barrel and a syringe plunger for advancement into the syringe barrel through the open proximal end. The foldable finger flange for the syringe comprises an attachment member configured to be removably mounted onto the syringe barrel flange, and a flange member pivotably attached to the attachment member. At least a portion of the flange member is pivotable between a use position, wherein said portion of the flange member extends generally perpendicular to the syringe barrel, thereby providing a flange having a greater extent than the syringe barrel flange, and a non-use position, wherein said portion of the flange member does not extend generally perpendicular to the syringe barrel.

BRIEF DESCRIPTION OF THE DRAWINGS

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings:

FIG. 4a is a front elevational view of the syringe of FIGS. 3a and 3b having the foldable finger flange of FIG. 1 mounted thereon in the use position;

FIG. 4b is a front and side perspective view of the syringe of FIGS. 3a and 3b having the foldable finger flange of FIG. 1 mounted thereon in the use position;

FIG. 10a is a front elevational view of the syringe having a foldable finger flange according to a second embodiment mounted thereon in the non-use position;

FIG. 10b is a front and side perspective view of the syringe having the foldable finger flange of FIG. 10a mounted thereon in the non-use position;

FIG. 11a is a front elevational view of the syringe having the foldable finger flange of FIG. 10a mounted thereon in the use position; and FIG. 11b is a front and side perspective view of a syringe having the foldable finger flange of FIG. 10a mounted thereon in the use position.

DESCRIPTION OF THE DISCLOSURE

Figure 1:
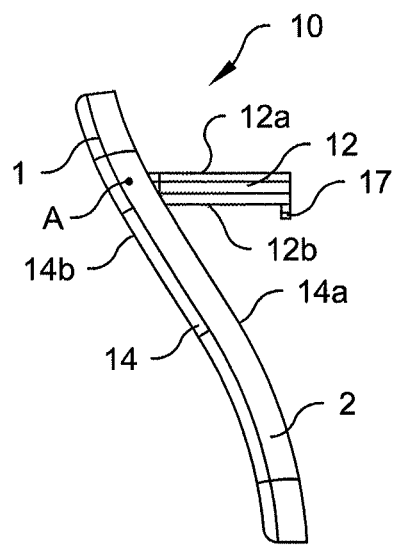
FIG. 1 is a side elevational view of a foldable finger flange, according to a first embodiment of the present disclosure, in a shipping/transport, non-use, position.

Certain terminology is used in the following description for convenience only and is not limiting. The words "lower,"

"bottom," "upper" and "top" designate directions in the drawings to which reference is made. The words "inwardly," "outwardly," "upwardly" and "downwardly" refer to directions toward and away from, respectively, the geometric center of the finger flange, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import: It should also be understood that the terms "about;" "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-9 a foldable finger flange, generally designated 10, according with a first embodiment of the present disclosure. The foldable finger flange 10 is an accessory or an adapter removably mountable onto a conventional syringe 50, i.e., a separate component from the syringe 50 that can be easily installed onto a portion of the syringe 50 and selectively removed therefrom. However, as should be understood by those of ordinary skill in the art, the foldable finger flange 10 may alternatively be permanently mounted onto the syringe 50 and/or be an integral component of the syringe 50. As should also be understood by those of ordinary skill in the art, and as shown best in FIG. 9, a conventional syringe 50 comprises a substantially cylindrical syringe barrel 52 having a syringe barrel flange 54 laterally extending from an open proximal end 52a of the syringe barrel 52 and a syringe plunger 56 for advancement into the syringe barrel 52 through the open proximal end 52a.

Figure 2A:
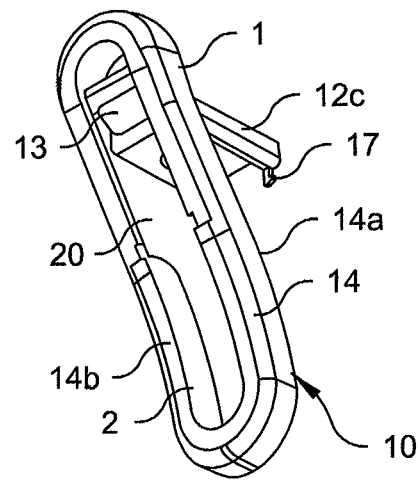
FIG. 2a is a perspective view of the bottom of the foldable finger flange of FIG. 1, in the non-use, position.
Figure 2B:
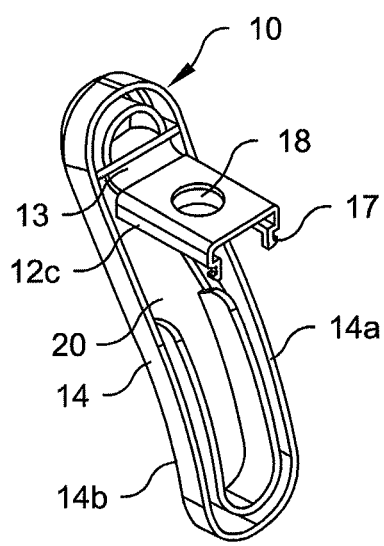
FIG. 2b is a perspective view of the top of the foldable finger flange of FIG. 1, in the non-use, position.
Figure 2C:
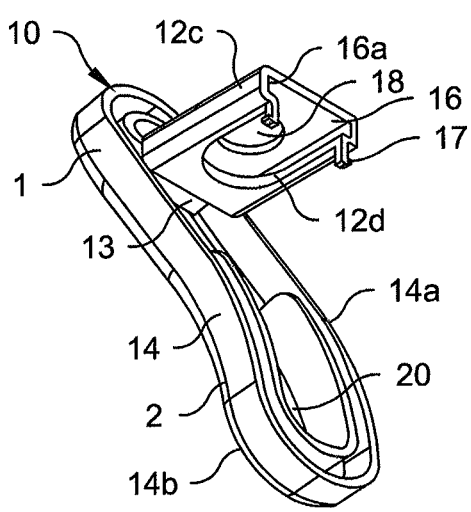
FIG. 2c is a second perspective view of the top of the foldable finger flange of FIG. 1, in the non-use, position, at a different angle.
Figure 2D:
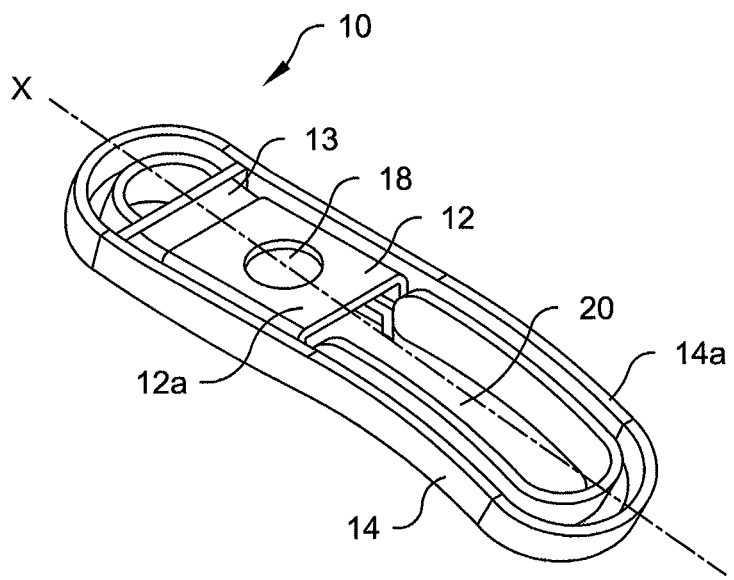
FIG. 2d is a third perspective view of the top of the foldable finger flange of FIG. 1, in the use, position, at another different angle.
Figure 2E:
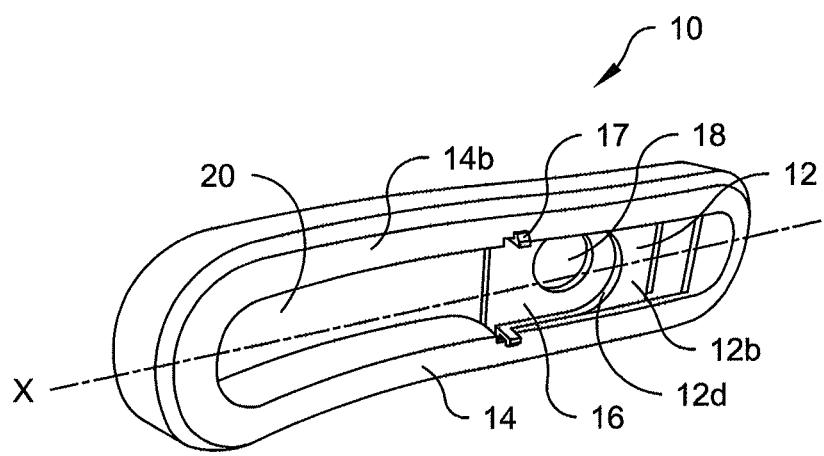
FIG. 2e is a perspective side view of the bottom of the foldable finger flange of FIG. 1, in a use position.

As shown in FIGS. 1-2e, the foldable finger flange 10 comprises an attachment member 12 pivotably attached to a flange member 14. In the illustrated embodiment, the attachment member 12 and the flange member 14 are integrally formed, e.g., a polymer molded in a single mold, and pivotably attached to one another via a living hinge 13, as shown best in FIG. 2b. Alternatively, the attachment member 12 and the flange member 14 may be formed of separate or individual components, made of multiple materials, and/or co-molded. For example, the flange member 14 may comprise several foldable parts capable of individual pivoting relative to the attachment member 12. The attachment member 12 and the flange member 14 may also be pivotably attached via any of numerous different conventional pivotable joints, such as, for example, without limitation, a hinge member, pin connection or a spring connection.

The attachment member 12 is configured to be removably mounted onto the syringe barrel flange 54. The attachment member 12 has a top surface 12a (shown best in FIGS. 2b and 2d), a bottom surface 12b (shown best in FIGS. 2c and 2e) and opposing sidewalls 12c connecting the top and bottom surfaces 12a, 12b. As shown, the living hinge 13 is attached to the top surface 12a of the attachment member 12. However, as should be understood, the hinge 13 may alternatively be attached to the bottom surface 12b of the attachment member 12. The surfaces 12a, 12b and 12c of the attachment member 12 define a first slot 16 (shown best in FIG. 2c) therebetween sized and shaped to receive the syringe barrel flange 54. The first slot 16 defines an open side end 16a for slidably receiving the syringe barrel flange 54. In one configuration, as shown in FIGS. 2a-5, the top surface 12a of the attachment member 12 includes an aperture 18 sized and shaped to receive the syringe plunger 56 therethrough. The bottom surface 12b of the attachment member 12 includes a generally U-shaped cutout 12d extending from the open side end 16a of the first slot 16 toward the opposing side wall 12c. The cutout 12d is sized and shaped to substantially fittingly receive a portion of the syringe barrel 52. Adjacent the cutout 12d, at the open side end 16a, is at least one tab 17 (two tabs 17 in the illustrated embodiment), extending generally perpendicularly away from the bottom surface 12b of the attachment member. The tabs 17 are configured to removably engage, such as via a snap fit, the flange member 14 when oriented in the use position, as described further below. However, as should be understood by those of ordinary skill in the art, the attachment member 12 and the flange member 14 may be removably engaged with one another when the flange member 14 is in the use position via a variety of engaging means, such as, for example via a pressure fit, opposing male and female mating geometry, magnets, or the like.

Figure 7:
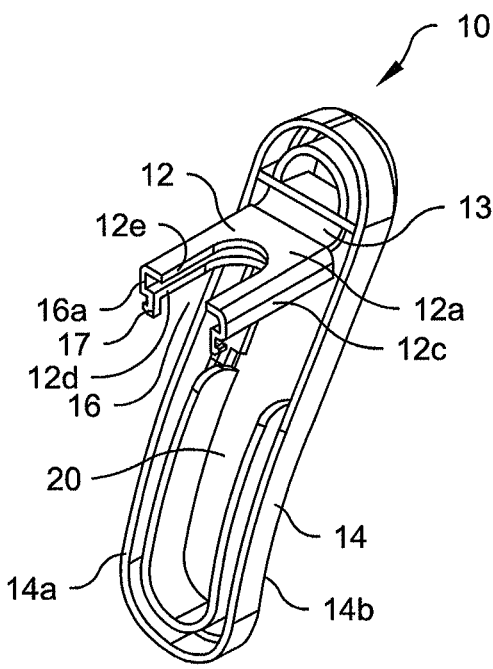
FIG. 7 is a perspective view of the top of the foldable finger flange of FIG. 1, in the non-use position, the attachment member having an alternative structure.

As shown in FIG. 7, the top surface 12a of the attachment member 12 may alternatively include a U-shaped cutout 12e, rather than the aperture 18, substantially identical to the U-shaped cutout 12d in the bottom surface 12b. That is, the cutout 12e also extends from the open side end 16a of the first slot 16 toward the opposing side wall 12c. The top cutout 12e is sized to receive a portion of the syringe plunger 56, and is substantially vertically aligned with the bottom cutout 12d.

Figures 5, 6:
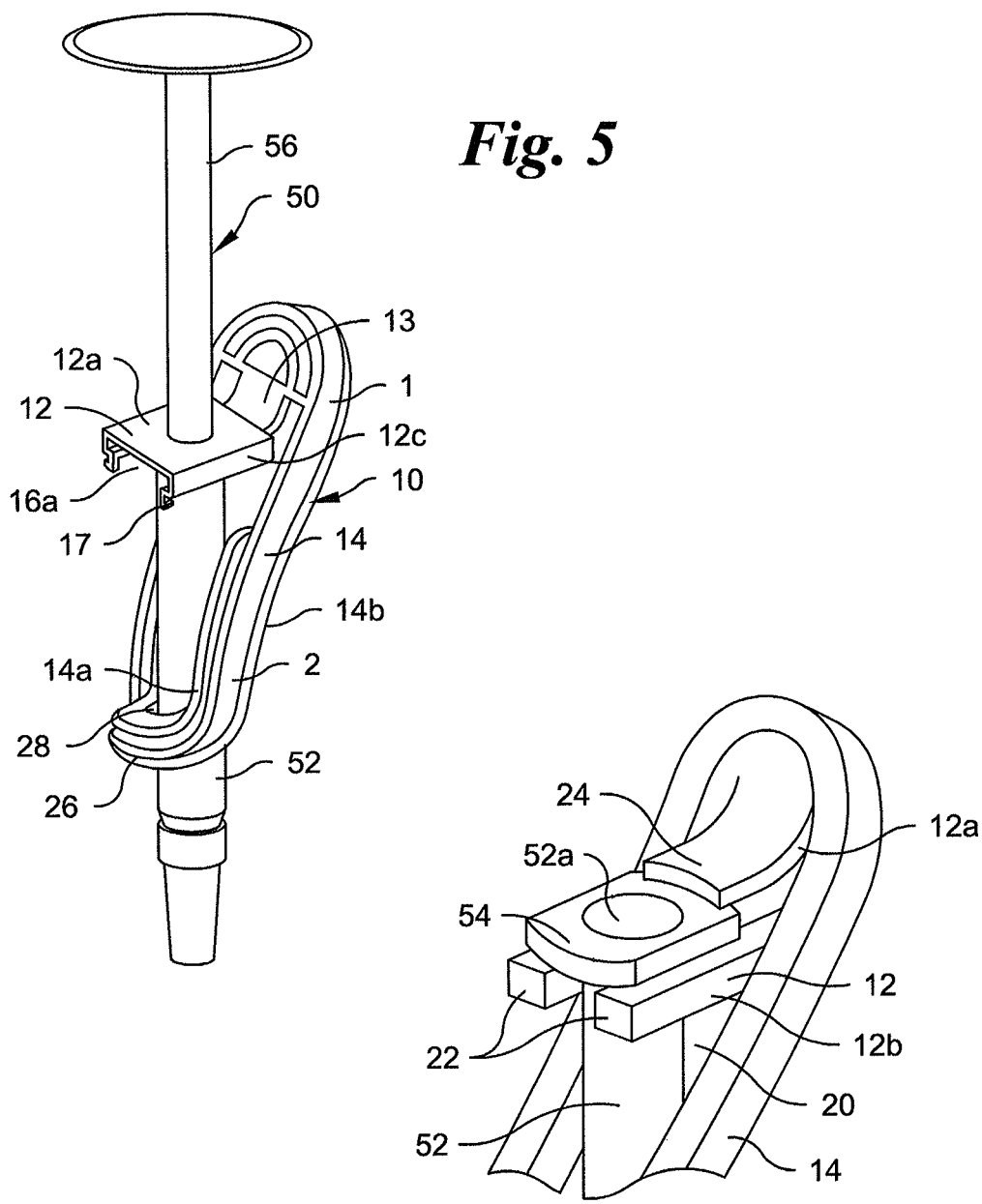
FIG. 5 is a front and side perspective view of a syringe having a foldable finger flange mounted thereon in the non-use position, the finger flange having an alternative structure.
FIG. 6 is an enlarged partial front and side perspective view of a syringe barrel having the foldable finger flange of FIG. 1 mounted thereon, the finger flange having an alternative attachment member.

As shown in FIG. 6, the bottom surface 12b of the attachment member 12 may alternatively include two laterally spaced apart prongs 22, and the top surface 12a of the attachment member 12 may include a generally central tab 24. The prongs 22 are laterally spaced apart to substantially fittingly receive the syringe barrel 52 therebetween, and also function as a support surface on which the syringe barrel flange 54 rests. The central tab 24 is vertically spaced from the prongs 22 to engage and substantially fittingly secure at least a portion of the syringe barrel flange 54 between the central tab 24 and the prongs 22. In the illustrated embodiment, the central tab 24 extends a distance sized to engage the syringe barrel flange 54 without covering the open proximal end 52a of the barrel 52 or interfering with the operation of the syringe plunger 56. However, as should be understood by those of ordinary skill in the art, the central tab 24 may alternatively extend an equal distance as the prongs 22 and include an aperture therein for advancing the syringe plunger 56 therethrough (not shown). In another alternative (not shown), the attachment member 12 may include a plurality of angularly spaced flexible tabs projecting from the top surface 12a, capable of snapping onto the syringe barrel flange 54.

Figure 3A:
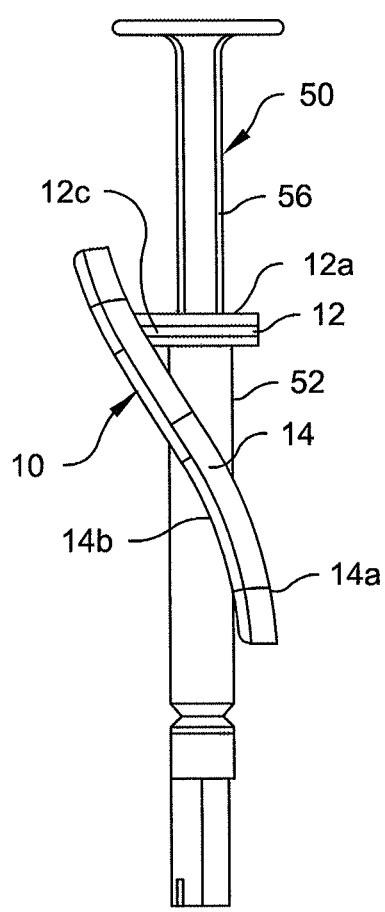
FIG. 3a is a front elevational view of a syringe having the foldable finger flange of FIG. 1 mounted thereon in the non-use position.
Figure 3B:
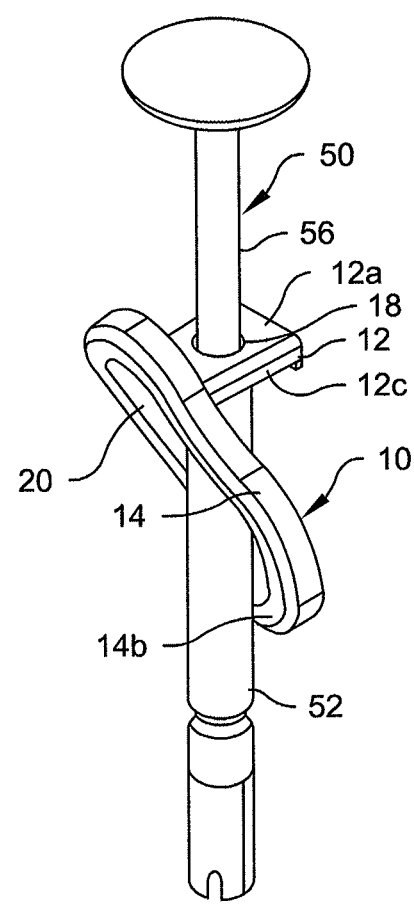
FIG. 3b is a front and side perspective view of the syringe of FIG. 3a having the foldable finger flange of FIG. 1 mounted thereon in the non-use position.

The flange member 14 is pivotable relative to the attachment member 12 between a use position (FIGS. 4a, 4b) and a non-use position (FIGS. 3a, 3b). In the use position, the flange member 14 extends generally perpendicularly to the syringe barrel 52, thereby providing a finger flange for a user having a greater extent than the syringe barrel finger flange 54. Thus, a user has a greater surface to engage and grip when using the syringe 50, thereby providing improved usability, leverage and control over the syringe 50. In the non-use position, the flange member 14 does not extend generally perpendicularly to the syringe barrel 52, but rather overlaps the barrel 52 and defines an acute angle with the barrel 52, as will be described further below, in order to decrease the footprint of the combined syringe 50 and finger flange 10.

As shown, the flange member 14 has a top surface 14a (shown best in FIGS. 2b and 2d) and a bottom surface 14b (shown best in FIGS. 2a and 2e), and defines a major axis X (shown best in FIGS. 2d and 2e). The flange member 14 further includes an internal second slot 20 extending along the major axis X, and completely between the top and bottom surfaces 14a, 14b. The second slot 20 is sized and shaped to receive the syringe barrel 52 therethrough. As shown best in FIGS. 3b and 4b, the second slot 20 receives the syringe barrel 52 therethrough in both the use position and the non-use position, and extends a length along the major axis X to permit the syringe barrel 52 to angularly slide through the second slot 20 during pivoting of the flange member 14 between the use and non-use positions, as will be explained further below. As also shown in FIG. 4b, the second slot 20 is also sized and shaped to receive the attachment member 12 when the flange member 14 is oriented in the use position, as also explained further below.

The flange member 14 is attached to, and pivotable about, the attachment member 12 at a pivot axis A, as shown in FIG. 1. As shown, the pivot axis A is spaced from both opposing ends of the flange member 14, along the major axis X. The flange member 14 defines a first section 1 on one side of the pivot axis A (shown in FIG. 1 as the section of the flange member 14 above the pivot axis A) and a second section 2 on the opposing side of the pivot axis A (shown in FIG. 1 as the section of the flange member 14 below the pivot axis A). As shown, the second section 2 is longer than the first section 1. When looking at flange member 14 in the use position from a side elevational view, as shown in FIG. 4a, the top surface 14a of the first section 1 of the flange member 14 has a slightly concave cross-sectional shape and the bottom surface 14b of the first section 1 has a slightly convex cross-sectional shape. Conversely, in the same orientation, the top surface 14a of the second section 2 of the flange member 14 has a slight convex cross-sectional shape and the bottom surface 14b of the second section 2 has a slightly concave cross-sectional shape. Therefore, the entirety of the flange member 14 defines a slight S-shape.

When the flange member 14 is pivoted from the use position (FIG. 4a) toward the non-use position (FIG. 3a), the first section 1 of the flange member 14 pivots toward the syringe plunger 56 and the second section 2 pivots toward the syringe barrel 52. The above-described slight S-shape of the flange member 14 curves the second section 2 of the flange member 14 toward the syringe barrel 52 in the non-use position. Thus, as shown best in FIG. 3a, at least a portion of the flange member 14 engages the syringe barrel 52 when oriented in the non-use position. Therefore, as should be understood, the slight S-shape of the flange member 14 results in a reduced footprint of the combined finger flange 10 and the syringe 50 when the flange member 14 is oriented in the non-use position, rather than a straight flange member. Accordingly, the finger flange 10 may be mounted onto the syringe 50 and shipped or transported with the flange member 14 in the non-use position, in a relatively smaller package.

In some embodiments, as shown in FIG. 5, at least the end portion 26 of the second portion 2 of the flange member 14 defines a complimentary contour to the syringe barrel 52 contour, such that the end portion of the flange member 14 complementarily engages the syringe barrel 52 when the flange member 14 is oriented in the non-use position. As shown in FIG. 5, the end portion 26 of the second portion 2 of the flange member 14 curves upwardly (to the left in FIG. 5) away from the top surface 14a of the flange member. The end portion 26 curves upwardly substantially perpendicularly relative to the major axis X of the flange member 14, resulting in a semi-circular slot 28, continuous with the second slot 20, at the end portion 26 that is oriented substantially perpendicularly to the syringe barrel 52 when the flange member is oriented in the non-use position. As the second slot 20 is sized and shaped to receive the syringe barrel 52, so is the slot 28, such that the slot 28 complementarily engages the syringe barrel 52, as shown in FIG. 5, when the flange member is oriented in the non-use position.

Figure 8A:
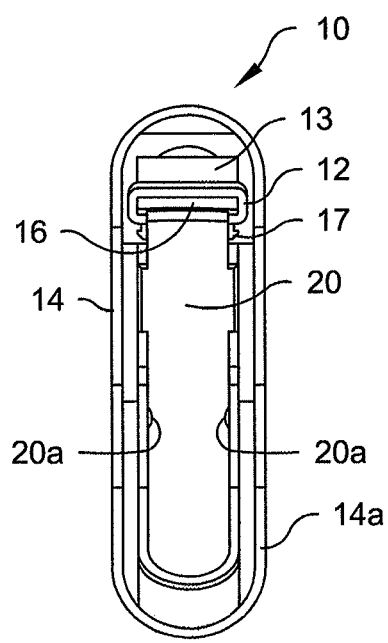
FIG. 8a is a front elevational view of the foldable finger flange of FIG. 1, wherein the flange member includes a pair of detents.
Figure 8B:
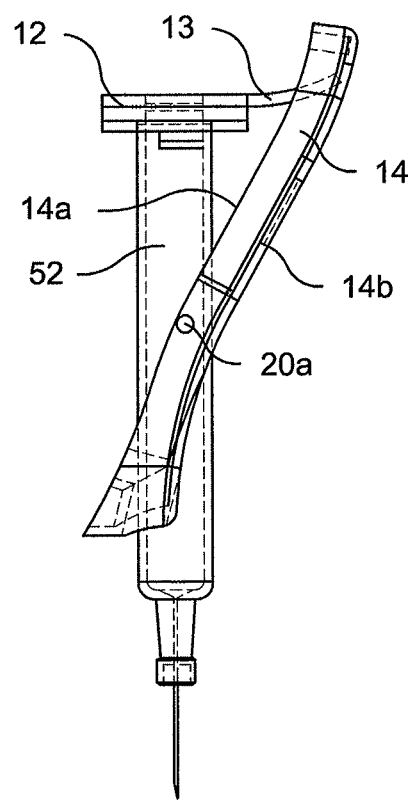
FIG. 8b is a rear elevational view of a syringe having the foldable finger flange of FIG. 8a mounted thereon, with the detents removably securing the flange member to the syringe barrel in the non-use position.

In some embodiments, as shown in FIG. 8A, the flange member 14 further includes at least one generally arcuate detent 20a, i.e., bump, projecting laterally inwardly into the internal second slot 20. As shown in FIG. 8A, the second slot 20 includes two aligned detents 20a on opposite sides of the second slot 20, projecting laterally inwardly. As shown in FIG. 8B, the detents 20a are configured to removably secure the flange member 14 to the syringe barrel 52 in the non-use position. When the flange member 14 is pivoted toward the non-use position and the detents 20a engage the syringe barrel 52, the syringe barrel 52 flexes the detents 20a around the diameter of the barrel 52. Once on the opposite side of the barrel 52 (relative to their location when the flange member 14 is in the use position), the detents 20a move back into their original orientation, thereby securing the flange member 14 in the non-use position. When ready for use, the flange member 14 may be manually pivoted back to the use position, thereby reversibly flexing the detents 20a relative to the syringe barrel 52.

Figure 9:
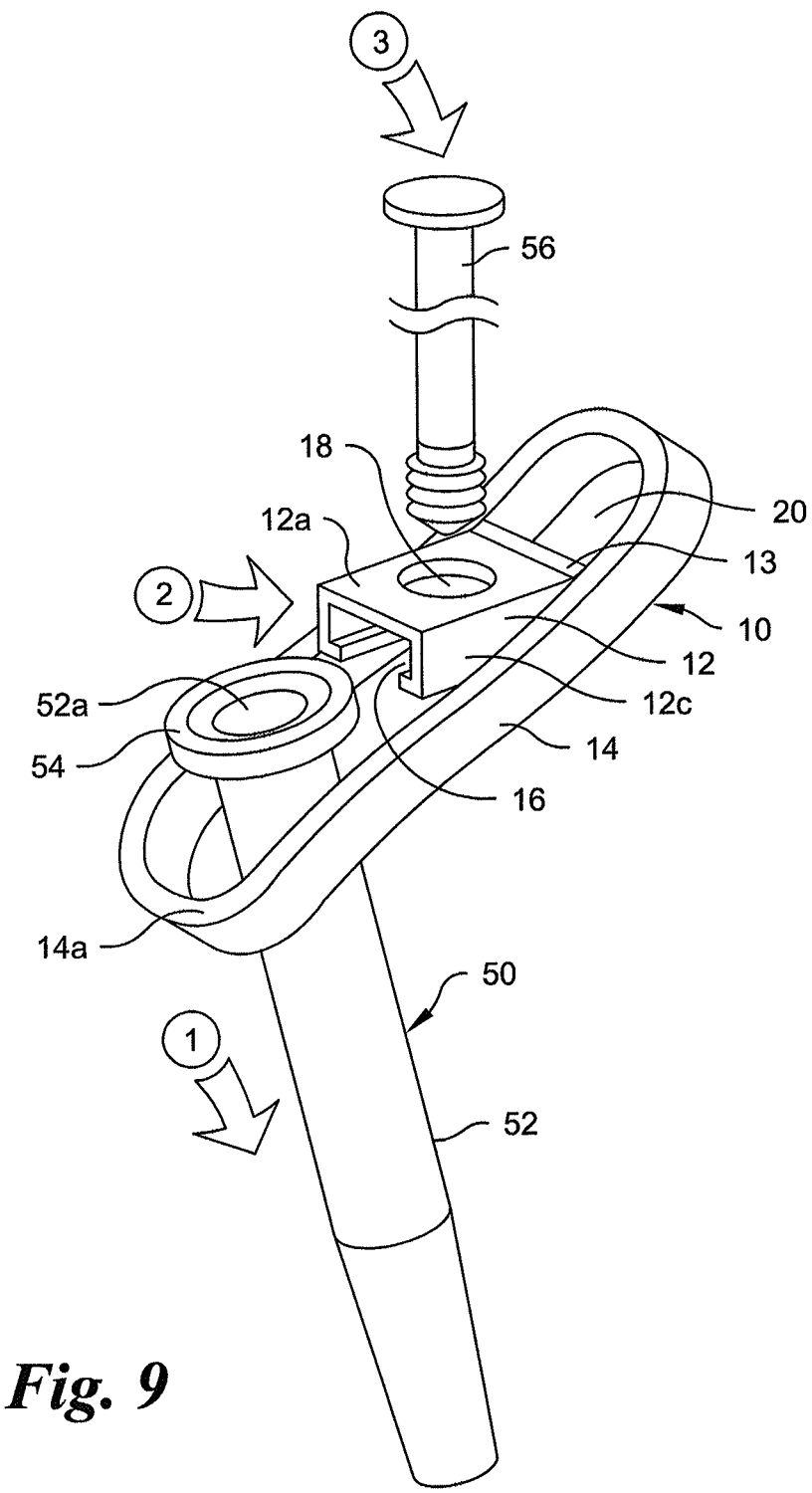
FIG. 9 illustrates the steps for a preferred method of mounting the foldable finger flange of FIG. 1 onto a syringe.

To mount the finger flange 10 onto a syringe 50, the syringe barrel 52 (with the syringe plunger 56 detached) is advanced through the second slot 20 of the second portion 2 of the flange member 14, as shown in step 1 of FIG. 9. In the illustrated embodiment, the flange member 14 is oriented between the use and non-use positions during step 1. Thereafter, when the syringe barrel 52 is approximately entirely advanced through the second slot 20, and the syringe barrel flange 54 is level with the attachment member 12, the syringe barrel flange 54 is slid into the first slot 16 of the attachment member 12, as shown in step 2 in FIG. 9, via the open side end 16a. When inserted into the first slot 16, the syringe barrel flange 54 rests on the bottom surface 12b of the attachment member 12, and the syringe barrel 52 extends therefrom, through the cutout 12d. The open proximal end 52a of the syringe barrel is also in vertical alignment with the aperture 18 of the attachment member 12. Lastly, as shown in step 3 in FIG. 9, the syringe plunger 56 is advanced through the aperture 18 of the attachment member 12 and into the syringe barrel 52, through the open proximal end 52a. Once the syringe plunger 56 is advanced through the aperture 18, the syringe plunger 56 prevents the attachment member 12 from separating from the syringe barrel flange 54. As should be understood however, where the attachment member 12 has a configuration as shown in FIG. 7, i.e., defines a top cutout 12e rather than the aperture 18, the syringe plunger 56 need not be removed from the syringe barrel 52 to mount the finger flange 10. Rather the syringe plunger 56 may already be inserted into the syringe barrel 52 prior to mounting the finger flange 10, and will slide through the top cutout 12e as the syringe barrel flange 54 is slid into the first slot 16 of the attachment member 12.

Once the finger flange 10 is mounted onto a syringe 50, the syringe 50 and the finger flange 10 can be packaged with the finger flange 10 in the non-use position (FIG. 3a), in order to minimize the packaging footprint. Thereafter, when the syringe 50 and the finger flange 10 are removed from the packaging for use, the flange member 14 is pivoted from the non-use position into the use position. As the flange member 14 approaches the use position, the attachment member 12 enters into the second slot 20 of the flange member 14 and the tabs 17 of the attachment member 12 are flexed inwardly by the bottom surface 14b of the flange member 14 bordering the second slot 20. When the flange member 14 reaches the use position, the tabs 17 snap onto the bottom surface 14b of the flange member 14, as shown in FIG. 2e, thereby releasably holding and maintaining the flange member 14 in the use position. In the use position, as shown in FIG. 4b, the top surface 12a of the attachment member 12 is substantially flush with the top surface 14a of the flange member 14, and at least a portion of the bottom surface 12b of the attachment member 12 abuts a portion of the bottom surface 14b of the flange member 14. As the bottom surface 12b of the attachment member 12 abuts the bottom surface 14b of the flange member 14, when the flange member 14 is oriented in the use position, the flange member 14 is prevented from pivoting, relative to the attachment member 12, past the use position, in a pivoting direction away from the non-use position.

Once the flange member 14 has been oriented in the use position, the syringe 50 effectively has a finger flange of a greater extent, providing a user with greater leverage and control over the syringe 50. The user may engage the flange with his/her fingers for improved usage of the syringe 50. After using the syringe 50, a user may desire to revert the flange member 14 back to the non-use position. To do so, the user pivots the flange member 14 from the use position to the non-use position with enough force to overcome the snap connection of the tabs 17 with the bottom surface 14b of the flange member 14, and then pivot the flange member 14 toward the non-use position. Alternatively a user may manually flex the tabs 17 inwards from their free end, to disconnect the snap connection, and then pivot the flange member 14 toward the non-use position. A user may also desire to remove the finger flange 10 from the syringe 50, e.g., to utilize with another syringe. Accordingly, a user will apply the reverse steps as applied for mounting the finger flange 10 onto the syringe 50 (FIG. 9), in the reverse order. Namely, the user will remove the syringe plunger 56 from the syringe barrel 52 and the attachment member 12, slide the syringe flange 54 out of the slot 16, and pull the syringe barrel 52 out of the second slot 20 of the flange member 14.

FIGS. 10a-11b show a second embodiment of the finger flange 110. The reference numerals of the second embodiment are distinguishable from those of the first embodiment by a factor of one-hundred (100), but otherwise indicate the same elements as indicated in the above-described first embodiment, except as otherwise specified. The finger flange 110 of the second embodiment is substantially similar to that of the first embodiment. The description of certain similarities between the embodiments may be omitted herein for the sake of brevity and convenience, and, therefore, is not limiting.

A distinguishing feature of the second embodiment is that the flange member 114 extends generally parallel to, and slightly spaced from, the syringe barrel 52 in the non-use position, as shown in FIGS. 10a and 10b, and the second slot 120 does not receive the syringe barrel 52 in the use position or the non-use position. As shown, the flange member 114 is located entirely to one side of the syringe 50 when in the non-use position. The second slot 120 is sized and shaped to approximately fittingly receive the attachment member 112 when the flange member 114 is oriented in the use position. Because the second slot 120 does not receive the syringe barrel 52, as in the first embodiment, and the second slot 120 need not extend the same length along the major axis A, but only to receive the attachment member 112.

As shown in FIGS. 10b and 11b, the outer end 130 of the first section 1 of the flange member 114 defines an opening 132. The opening 132 extends completely through the outer end 130, i.e., the second slot 120 is in communication with the exterior of the outer end 130. The opening 132 is sized and shaped to slidably receive the syringe plunger 56 therethrough during pivoting of the flange member 114 between the use and non-use positions.

As the second slot 120 does not receive the syringe barrel 52, a syringe barrel flange 54 is directly inserted into the first slot 116 of the attachment member 112 to mount the finger flange 110 onto a syringe 50. Thereafter, the leading end of the syringe plunger 56 is advanced through the aperture 118 and into the syringe barrel 52, through the open proximal end 52a to releasably hold the finger flange 110 on the syringe 50.

When the syringe 50 is ready for use, a user may pivot the flange member 114 from the non-use position (FIGS. 10a, 10b) to the use position (FIGS. 11a, 11b). During pivoting, the flange member 114 crosses over the syringe plunger 56. To cross over the syringe plunger 56, the plunger 56 passes through the opening 132 and into the second slot 120 of the flange member. When the flange member 114 reaches the use position, the flange member 114 releasably locks in place in engagement with the attachment member 112. For example, similarly to the above-described first embodiment, tabs (not shown) extending from the attachment member 112, may snap onto the flange member 114, thereby releasably holding and maintaining the flange member 14 in the use position. Once the flange member 114 is in the use position, it is ready for use, with the same advantages as explained above.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

We claim:

1. A foldable finger flange for a syringe including a syringe barrel having a syringe barrel flange laterally extending from an open proximal end of the syringe barrel and a syringe plunger for advancement into the syringe barrel through the open proximal end, the foldable finger flange comprising:
    an attachment member configured to be removably mounted onto the syringe barrel flange, and
    a flange member pivotably attached to the attachment member, wherein at least a portion of the flange member is pivotable between a use position, wherein the attachment member is mounted onto the syringe barrel flange and said portion of the flange member extends generally perpendicular to the syringe barrel, thereby providing a flange having a greater extent than the syringe barrel flange, and a non-use position, wherein the attachment member is mounted onto the syringe barrel flange and said portion of the flange member does not extend generally perpendicular to the syringe barrel, and wherein the flange member defines a major axis and includes an internal slot extending along the major axis, said internal slot being sized and shaped to receive the attachment member when the flange member is oriented in the use position.

2. The foldable finger flange of claim 1, wherein the attachment member comprises a top surface, a bottom surface, and opposing side walls connecting the top and bottom surfaces and defining a first slot therebetween having an open side end for slidably receiving the syringe barrel flange, wherein the top surface includes (i) an aperture sized and shaped to receive the syringe plunger therethrough or (ii) a cutout extending from the open side end of the first slot toward the opposing side wall, sized to receive a portion of the syringe plunger, and the bottom surface includes a cutout extending from the open side end of the first slot toward the opposing side wall, sized and shaped to substantially fittingly receive a portion of the syringe barrel.

3. The foldable finger flange of claim 2, wherein the top surface cutout and the bottom surface cutout comprise substantially similar generally U-shaped openings.

4. The foldable finger flange of claim 2, wherein the flange member comprises a top surface and a bottom surface, and at least a portion of the bottom surface of the attachment member abuts at least a portion of the bottom surface of the flange member in the use position, such that the attachment member serves as a stop to prevent pivoting of the flange member beyond the use position when pivoting away from the non-use position.

5. The foldable finger flange of claim 1, wherein the slot of the flange member is sized and shaped to receive the syringe barrel therethrough.

6. The foldable finger flange of claim 5, wherein the internal slot receives the syringe barrel therethrough in both the use position and the non-use position of the flange member, and the internal slot extends a length along the major axis to permit the syringe barrel to angularly slide through the internal slot during pivoting of the flange member between the non-use position and the use position.

7. The foldable finger flange of claim 5, wherein the flange member further includes at least one generally arcuate detent projecting laterally inwardly into the internal slot, said at least one arcuate detent being configured to engage, and flex around a diameter of the syringe barrel during pivoting of the flange member from the use to the non-use position, to, in turn, removably secure the flange member to the syringe barrel in the non-use position.

8. The foldable finger flange of claim 7, wherein the at least one detent comprises two aligned detents on opposing sides of the internal slot.

9. The foldable finger flange of claim 1, wherein at least a portion of the flange member engages the syringe barrel when in the non-use position.

10. The foldable finger flange of claim 1, wherein a portion of the flange member defines a complementary contour to a contour of the syringe barrel, the portion of the flange member complementarily engaging the syringe barrel in the non-use position.

11. The foldable finger flange of claim 1, wherein the flange member has a first end at one end of the flange member along the major axis and a second end at an opposing end of the flange member along the major axis, and the flange member is attached to the attachment member at a pivot axis, said pivot axis being spaced from both the first end and the second end of the flange member.

12. The foldable finger flange of claim 1, wherein the flange member extends generally parallel to the syringe barrel in the non-use position.

13. The foldable finger flange of claim 12, wherein the flange member comprises a first end at one end of the flange member along the major axis, a second end at an opposing end of the flange member along the major axis, wherein said second end includes an opening extending from the internal slot to an exterior of the second end, said opening being sized and shaped to slidably receive the syringe plunger therethrough during movement of the flange member between the non-use and use positions.

14. The foldable finger flange of claim 1, wherein a bottom surface of the attachment member comprises two laterally spaced apart prongs and a top surface of the attachment member comprises one generally central tab, wherein the two prongs are laterally spaced apart to fittingly receive the syringe barrel therebetween, and the central tab is vertically spaced from the prongs to fittingly receive at least a portion of the syringe barrel flange therebetween.

15. The foldable finger flange of claim 1, wherein the attachment member and the flange member are integrally formed, and are pivotably attached to one another via a living hinge.

16. A foldable finger flange for a syringe including a syringe barrel having a syringe barrel flange laterally extending from an open proximal end of the syringe barrel and a syringe plunger for advancement into the syringe barrel through the open proximal end, the foldable finger flange comprising:
an attachment member comprising a top surface, a bottom surface, and opposing side walls connecting the top and bottom surfaces and defining a first slot therebetween having an open side end for slidably receiving the syringe barrel flange, the top surface including (i) an aperture sized and shaped to receive the syringe plunger therethrough or (ii) a cutout extending from the open side end of the first slot toward the opposing side wall, sized to receive a portion of the syringe plunger, and the bottom surface including a cutout extending from the open side end of the first slot toward the opposing side wall, sized and shaped to substantially fittingly receive a portion of the syringe barrel, the attachment member being configured to be removably mounted onto the syringe barrel flange, and
a flange member pivotably attached to the attachment member, wherein at least a portion of the flange member is pivotable between a use position, wherein said portion of the flange member extends generally perpendicular to the syringe barrel, thereby providing a flange having a greater extent than the syringe barrel flange, and a non-use position, wherein said portion of the flange member does not extend generally perpendicular to the syringe barrel,
wherein the flange member comprises a top surface and a bottom surface and the attachment member further comprises at least one tab extending away from the bottom surface of the attachment member, wherein said at least one tab is configured to removably snap onto the bottom surface of the flange member when the flange member is oriented in the use position to maintain the flange member in the use position.

17. The foldable finger flange of claim 16, wherein the at least one tab extends generally perpendicularly away from the bottom surface of the attachment member.

18. A foldable finger flange for a syringe including a syringe barrel having a syringe barrel flange laterally extending from an open proximal end of the syringe barrel and a syringe plunger for advancement into the syringe barrel through the open proximal end, the foldable finger flange comprising:
an attachment member configured to be removably mounted onto the syringe barrel flange, and
a flange member pivotably attached to the attachment member, wherein at least a portion of the flange member is pivotable between a use position, wherein said portion of the flange member extends generally perpendicular to the syringe barrel, thereby providing a flange having a greater extent than the syringe barrel flange, and a non-use position, wherein said portion of the flange member does not extend generally perpendicular to the syringe barrel, wherein the flange member is attached to the attachment member at a pivot axis, and the flange member defines a first section on one side of said pivot axis, having a top surface and a bottom surface, and a second section on an opposing side of said pivot axis, having a top surface and a bottom surface, wherein the first section pivots toward the syringe plunger and the second section pivots toward the syringe barrel when the flange member is pivoted from the use position to the non-use position, and wherein the top surface of the first section has a slightly concave cross-sectional shape, the bottom surface of the first section has a slightly convex cross-sectional shape, the top surface of the second section has a slightly convex cross-sectional shape and the bottom surface of the second section has a slightly concave cross-sectional shape.

* * * * *